US012605317B2

(12) United States Patent
Choi et al.

(10) Patent No.: US 12,605,317 B2
(45) Date of Patent: Apr. 21, 2026

(54) WATER-IN-OIL MAKEUP COSMETIC COMPOSITION HAVING WATER RESISTANCE AND CLEANSING PROPERTIES

(71) Applicant: LG HOUSEHOLD & HEALTH CARE LTD., Seoul (KR)

(72) Inventors: Min-Sung Choi, Seoul (KR); Seung-Jin Song, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 283 days.

(21) Appl. No.: 18/274,638

(22) PCT Filed: Jan. 19, 2022

(86) PCT No.: PCT/KR2022/000976
§ 371 (c)(1),
(2) Date: Jul. 27, 2023

(87) PCT Pub. No.: WO2022/164117
PCT Pub. Date: Aug. 4, 2022

(65) Prior Publication Data
US 2024/0091116 A1        Mar. 21, 2024

(30) Foreign Application Priority Data
Jan. 28, 2021     (KR) ........................ 10-2021-0012626

(51) Int. Cl.
*A61K 8/36*          (2006.01)
*A61K 8/06*          (2006.01)
(Continued)

(52) U.S. Cl.
CPC .............. *A61K 8/361* (2013.01); *A61K 8/064* (2013.01); *A61K 8/20* (2013.01); *A61K 8/29* (2013.01);
(Continued)

(58) Field of Classification Search
None
See application file for complete search history.

(56) References Cited

U.S. PATENT DOCUMENTS 5,560,917 A  *  10/1996  Cohen .................... A61Q 17/04
424/59
2006/0024375 A1     2/2006  Hasegawa et al.

FOREIGN PATENT DOCUMENTS

JP          1-172312 A       7/1989
JP      2002-220320 A       8/2002
(Continued)

OTHER PUBLICATIONS

KR20100135537—EPO English translation (Year: 2010).*
(Continued)

*Primary Examiner* — Kyung S Chang
(74) *Attorney, Agent, or Firm* — Birch, Stewart, Kolasch & Birch, LLP

(57) ABSTRACT

The present disclosure provides a water-in-oil makeup cosmetic composition containing isostearic acid, a pigment-grade powder (specifically, a pigment-grade powder coated with a lipoamino acid), an emulsifier having an HLB greater than 0 and lower than or equal to 8, and a residual amount of water, the composition having superior water resistance and cleansing properties at the same time. The water-in-oil makeup cosmetic composition of the present disclosure can be usefully used because it has superior water resistance in environments with below-neutral pH, such as tap water, sweat, etc. and is converted to have superior cleansing properties when the skin is washed with alkaline water such as soapy water.

12 Claims, 4 Drawing Sheets

(51) Int. Cl.

| *A61K 8/20* | (2006.01) |
|---|---|
| *A61K 8/27* | (2006.01) |
| *A61K 8/29* | (2006.01) |
| *A61K 8/44* | (2006.01) |
| *A61K 8/49* | (2006.01) |
| *A61Q 1/12* | (2006.01) |

(52) U.S. Cl.
  CPC ............ *A61Q 1/12* (2013.01); *A61K 2800/43*
    (2013.01); *A61K 2800/52* (2013.01); *A61K*
    *2800/622* (2013.01)

(56) References Cited

FOREIGN PATENT DOCUMENTS

| JP | 2004-161655 A | 6/2004 |
|---|---|---|
| JP | 2004-231564 A | 8/2004 |
| JP | 2008-50310 A | 3/2008 |
| JP | 2012-240999 A | 12/2012 |
| JP | 2014-221910 A | 11/2014 |
| JP | 2018-177736 A | 11/2018 |
| JP | 2019-14709 A | 1/2019 |
| KR | 10-2010-0135537 A | 12/2010 |
| KR | 10-2013-0127463 A | 11/2013 |

OTHER PUBLICATIONS

JP2004-231564A—Google English translation (Year: 2004).*
International Search Report (PCT/ISA/210) issued in PCT/KR2022/
00976 dated May 2, 2022.

* cited by examiner

FIG. 1
| | WATER RESISTANCE | EASINESS OF CLEANSING |
|---|---|---|
| CONVENTIONAL COMPOSITION | PLAIN WATER | SOAPY WATER |
| EXAMPLE OF THE PRESENT DISCLOSURE | PLAIN WATER | SOAPY WATER |
FIG. 2
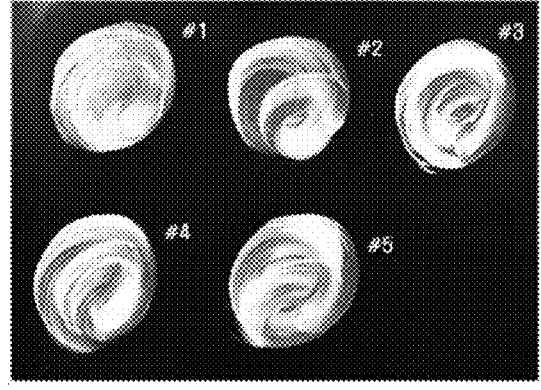
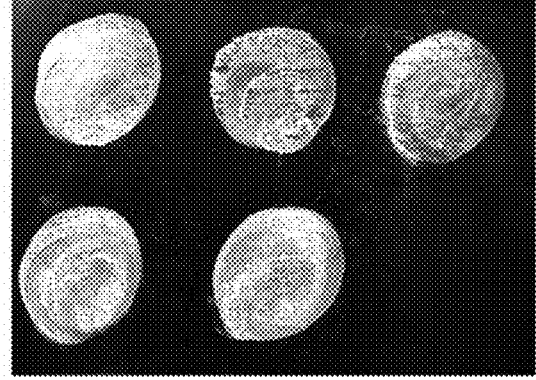

WATER-IN-OIL MAKEUP COSMETIC COMPOSITION HAVING WATER RESISTANCE AND CLEANSING PROPERTIES

The present application claims priority to Korean Patent Application No. 10-2021-0012626 filed on Jan. 28, 2021 in the Republic of Korea, the disclosures of which are incorporated herein by reference.

The present disclosure relates to a water-in-oil makeup cosmetic composition. More specifically, it relates to a water-in-oil makeup cosmetic composition which has superior water resistance and superior cleansing properties at the same time.

BACKGROUND ART

Makeup products are used to hide skin defects and create an even skin tone. These makeup products use high contents of pigments to create skin colors. In general, they are made in the form of W/O emulsions that have superior adhesivity to the skin and good makeup durability.

However, the W/O-type cosmetics containing high contents of pigments are inconvenient in that the removal of the cosmetics is not easy. In particular, powders for pigments, which are in solid states, not only feel like foreign materials on the skin but also clog pores and cause troubles. In addition, since they are highly visible, it is very important to improve the cleansing properties of makeup products. Therefore, double cleansing is necessary to remove the makeup products in general.

Recently, in several results of investigating skin condition after double cleansing, it has been confirmed that double cleansing not only causes barrier damage due to strong skin friction but also causes dryness by inhibiting the skin-moisturizing effect.

In this regard, in Korean Patent Registration No. 1342231, a powder that has water resistance in water with neutral pH but is removed easily in soapy water with high pH was developed by using a powder whose surface properties change depending on external pH conditions by coating the surface of the powder with a pH-sensitive polymer. However, this technology is limited only to the improvement of the cleansing properties of the powder itself and it has the disadvantage that the removal of the makeup is not easy.

Therefore, it is necessary to develop a makeup product that has both water resistance during use and cleansing properties that allows easy removal with only one cleansing step.

DISCLOSURE

Technical Problem

The present disclosure is directed to providing a water-in-oil makeup cosmetic composition having superior water resistance and cleansing properties at the same time. More specifically, it is directed to providing a water-in-oil makeup cosmetic composition that can be removed easily with only one cleansing step.

Technical Solution

In an aspect, the present disclosure provides a water-in-oil makeup cosmetic composition comprising isostearic acid, a pigment-grade powder, an emulsifier having an HLB greater than 0 and lower than or equal to 8, and a residual amount of water, wherein the composition is washed off better with an alkaline pH aqueous solution than with a neutral pH aqueous solution.

The inventors of this application have found out that a water-in-oil (W/O-type) makeup product having the above-described composition is resistant to water and sweat and has high makeup durability, but can be removed easily with only one cleansing step due to improved cleansing properties, and have completed the present disclosure. In particular, the inventors of the present disclosure have discovered that a cosmetic product containing a pigment-grade powder at a high content has remarkably excellent cleansing power as compared to other compositions, when the above composition is satisfied, and have completed the present disclosure.

As shown in FIG. 1, the cosmetic composition of the present disclosure has superior water resistance in neutral aqueous solutions with a pH of $7\pm0.5$, such as tap water, but is washed off well with an alkaline solution with a pH of, e.g., 9-11.

In a specific exemplary embodiment of the present disclosure, in the composition of the present disclosure, the isostearic acid may be contained in an amount of 1-40 wt % based on the total weight of the composition, the pigment-grade powder may be contained in an amount of 1-40 wt % based on the total weight of the composition, and the emulsifier having an HLB greater than 0 and lower than or equal to 8 may be contained in an amount of 0.1-10 wt % based on the total weight of the composition.

The composition of the present disclosure contains isostearic acid. Surprisingly, the inventors of the present disclosure have newly found out that isostearic acid exhibits remarkably excellent effect as compared to other solid fatty acids in compositions containing a pigment-grade powder at a high content.

The isostearic acid may be contained in an amount of 1-40 wt %, specifically 3-40 wt %, more specifically 5-40 wt %, further more specifically 7-40 wt %, based on the total weight of the composition. If the content of the isostearic acid is too low, the desired effect is low.

The composition of the present disclosure contains a pigment-grade powder for correcting skin tone.

Specifically, the pigment-grade powder may be titanium dioxide, talc, tin oxide or a mixture thereof having a pigment-grade powder size. More specifically, the pigment-grade powder of the present disclosure is titanium dioxide.

In the present disclosure, the term "pigment-grade powder" means a powder having a powder size of 200-1000 nm, specifically 250-900 nm, more specifically 300-800 nm. A powder having a powder size smaller than 100 nm or smaller than 200 nm is mainly used to absorb light in the ultraviolet range, but it is difficult to expect the change in skin tone when applied onto the skin because it is relatively transparent since its property of scattering light in the visible range is weak.

That is to say, in the present disclosure, the pigment-grade powder is a powder that causes the change in skin tone by scattering light in the visible range when applied onto the skin, and may be used as a colorant or a pigment.

More specifically, the pigment-grade powder contained in the composition of the present disclosure is a pigment-grade powder coated with a lipoamino acid, particularly a $TiO_2$ powder coated with a lipoamino acid. The pigment-grade powder coated with a lipoamino acid improves water resistance at neutral pH by maintaining its shape and also improves cleansing properties at high pH by affecting the coating.

Typically, the pigment-grade powder may be surface-treated to increase oil dispersibility, and the materials used for the surface treatment include dimethicone, triethoxy-caprylylsilane, fatty acids, lipoamino acids, etc., although not being limited thereto.

The inventors of the present disclosure have evaluated the cleansing properties of various types of pigment-grade powders. As a result, they have found that a pigment-grade powder coated with a lipoamino acid has oil-dispersible properties in neutral (pH 7) water, but exhibits water-dispersible properties in alkaline water (e.g., pH 10) such as soapy water as the coating material is dissociated. It is because the surface properties of the lipoamino acid are changed under alkaline conditions, unlike dimethicone, tri-ethoxycaprylylsilane, fatty acids, etc. used for powder coat-ing. These properties can make the composition be resistant to water and sweat but have improved cleansing properties in soapy water. In addition, as powder with a size smaller than 100 nm is transparent and invisible, when applied to the skin it is difficult to feel the cleansing effect. Powder with the size as the pigment-grade results in a white turbidity phe-nomenon when applied to the skin, so coating such powder with lipoamino acid is more suitable and ideal for makeup products.

In the present disclosure, the lipoamino acid according to the present disclosure may be palmitoyl proline, magnesium palmitoyl glutamate, sodium palmitoyl sarcosinate, dipalmi-toylhydroxyproline, palmitoylisoleucine, capryloylglycine, dioctyldodecyllauroyl glutamate, cholesteryl/behenyl/octyl-dodecyllauroyl glutamate, cholesteryl/octyldodecyllauroyl glutamate, phytosteryl/behenyl/octyldodecyllauroyl gluta-mate, phytosteryl/octyldodecyllauroyl glutamate, phytos-teryl/decyltetradecylmyristoylmethyl alaninate or a mixture thereof, specifically palmitoyl proline, magnesium palmitoyl glutamate, sodium palmitoyl sarcosinate or a mixture thereof.

In the present disclosure, the pigment-grade powder coated with a lipoamino acid may be contained in an amount of 1-40 wt % based on the total weight of the composition. The pigment-grade powder coated with a lipoamino acid may be contained in an amount of specifically 3-40 wt %, more specifically 5-30 wt %, further more specifically 7-20 wt %. If the content of the pigment-grade powder coated with a lipoamino acid is too low, its effect may be insig-nificant. And, if the content is too high, it may be difficult to maintain stability and stiff feeling or white turbidity may occur.

The composition of the present disclosure may further contain a powder other than the pigment-grade powder coated with a lipoamino acid within a range not negatively affecting the purpose of the present disclosure. For example, a powder such as talc, tin oxide, mica, silica, PMMA, etc. may be further contained.

The composition of the present disclosure also contains an emulsifier for preparing a water-in-oil (W/O-type) compo-sition. In particular, it contains an emulsifier having an HLB greater than 0 and lower than or equal to 8. Specifically, the emulsifier contained in the composition of the present dis-closure may have an HLB of 8 or lower, specifically 7 or lower, more specifically 6 or lower.

In an aspect of the present disclosure, the emulsifier may be contained in an amount of 0.1-10 wt % based on the total weight of the composition.

In the present disclosure, the emulsifier may be a sorbitan fatty acid ester such as sorbitan monolaurate, sorbitan monoisostearate, sorbitan tristearate, sorbitan olivate, etc.; a glycerin fatty acid ester such as glycerol monostearate, glycerol monooleate, etc.; a polyoxyethylene hydrogenated castor oil such as POE(5) hydrogenated castor oil, POE(7.5) hydrogenated castor oil, POE(10) hydrogenated castor oil, etc.; a polyether-modified silicone surfactant such as PEG-9 polydimethylsiloxyethyl dimethicone, lauryl PEG-9 polydi-methylsiloxyethyl dimethicone, polyglyceryl-3polydimeth-ylsiloxyethyl dimethicone, lauryl polyglyceryl-3-polydim-ethylsiloxyethyl dimethicone, PEG-11 methyl ether dimethicone, PEG-10 dimethicone, cetyl PEG/PPG-10/1 dimethicone, PEG/PPG-20/22 butyl ether dimethicone and dimethicone/PEG-10/15 crosspolymer; a polyglyceryl fatty acid ester such as dimethicone polyol, polyglyceryl-2 ses-quioleate, polyglyceryl-10 pentaoleate, polyglyceryl-5 hex-astearate, polyglyceryl-4 diisostearate/polyhydroxystearate/sebacate copolymer and diisostearoyl polyglyceryl-3 dimer dilinoleate; or a mixture thereof.

In an aspect of the present disclosure, the present disclo-sure composition may further contain a monovalent ionic salt as a stabilizer. The stabilizer according to the present disclosure improves the stability of the W/O-type emulsion composition.

Sodium chloride may be used as the monovalent ionic salt.

In general, a divalent ionic salt such as magnesium sulfate, calcium chloride, etc. may also be used as a stabi-lizer in the W/O-type emulsion. However, since the divalent ionic salt may form an insoluble precipitate with the com-ponent contained in the composition of the present disclo-sure, it is more preferred to use a monovalent ionic salt in order not to impair the effect of the present disclosure. However, the present disclosure is not limited by this theoretical mechanism.

Accordingly, in an aspect, the composition according to the present disclosure does not substantially contain a diva-lent ionic salt such as ZnO, etc. For example, the compo-sition according to the present disclosure contains a divalent ionic salt such as ZnO, etc. in an amount of 0-5 wt %, specifically 0-3 wt %, more specifically 0-1 wt %, based on the total weight of the composition. And, further more specifically, it contains no divalent ionic salt.

In addition, the water-in-oil makeup cosmetic composi-tion according to the present disclosure may contain the components commonly used in cosmetic compositions in the art within ranges not negatively affecting the purpose of the present disclosure. For example, it may further contain an emollient, an (organic) UV blocker, a moisturizer, a thickener, a preservative, a fragrance, etc.

In the present disclosure, as the emollient, an ester-based oil such as caprylic/capric triglyceride, dicaprylyl carbonate, neopentyl glycol dicaprate, 2-octyldodecyl myristate, iso-propyl myristate, isocetyl ethylhexanoate, pentaerythrityl tetraethylhexanoate, butylene glycol dicaprylate/caprate, hexyl laurate, distearyl maleate, cetyl 2-ethylhexanoate, octyldodecanol, glyceryl triethylhexanoate, etc.; a silicone oil such as cyclopentasiloxane, dimethylpolysiloxane, meth-ylphenylpolysiloxane, decamethylcy cl op entasil oxane, methyl trimethicone, phenyl trimethicone, cyclomethicone, dimethicone, etc.; a hydrocarbon-based oil such as isohexa-decane, squalane, mineral oil, hydrogenated polydecene, hydrogenated polyisobutene, etc.; a vegetable oil such as olive oil, avocado oil, jojoba oil, macadamia oil, shea butter, mango butter, murumuru butter, cocoa butter etc., and the like may be used, although not being limited thereto.

In the present disclosure, as the UV blocker, ethylhexyl methoxycinnamate, ethylhexyl salicylate, bis-ethylhexy-loxyphenol methoxyphenyl triazine, diethylamino hydroxy-benzoyl hexyl benzoate, octocrylene, butyl methoxydibenzoylmethane, oxybenzone, octyltriazone, menthyl anthranilate, phenylbenzimidazole sulfonic acid, 2-hydroxy-4-methoxybenzophenone sulfonic acid, 3-(4-methylbenzylidene)camphor, isoamyl p-methoxycinnamate, homosalate, drometrizole trisiloxane, benzophenone-3, ethylhexyl triazone, DEA-methoxycinnamate, disodium phenyl dibenzimidazole tetrasulfonate, benzophenone-8, TEA salicylate, butyl methoxydibenzoylmethane, ethylhexyl dimethyl PABA, etc. may be used, although not being limited thereto.

In the present disclosure, as the moisturizer, 1,3-butylene glycol, 2,3-butylene glycol, propylene glycol, dipropylene glycol, pentylene glycol, betaine, trehalose, glycerin, sorbitol, propanediol, 1,2-hexanediol, octanediol, etc. may be used, although not being limited thereto.

In the present disclosure, as the thickener, bentone, dextrin palmitate, polyamide-8, etc. may be used, although not being limited thereto.

In the present disclosure, as the preservative, phenoxyethanol, paraben, paraoxybenzoic acid ester, sodium benzoate, sorbic acid, potassium sorbate, salicylic acid, benzalkonium chloride, trichlorocarbanilide, etc. may be used, although not being limited thereto.

The contents of all the components described in the present disclosure do not exceed the maximum amounts specified by the related laws and regulations of Korea, China, the US, Europe, Japan, etc. (e.g., Regulations on the Safety Standards, Etc. of Cosmetics (Korea), Cosmetic Safety Technical Specifications (China) or Hygiene Specifications (China)). That is to say, the cosmetic composition according to the present disclosure contains the components according to the present disclosure within the content limits allowed in the related laws and regulations of each country.

Advantageous Effects

The present disclosure provides a water-in-oil makeup cosmetic composition having superior water resistance and cleansing properties at the same time. More specifically, the present disclosure provides a water-in-oil makeup cosmetic composition which is resistant to water and sweat and has high makeup durability, but can be removed easily with only one cleansing step.

DESCRIPTION OF DRAWINGS

FIG. 1 compares the effect of a composition according to the present disclosure and a conventional composition.

FIG. 2 shows a result of evaluating the water resistance of compositions #1 to #5.

BEST MODE

Figure 3:
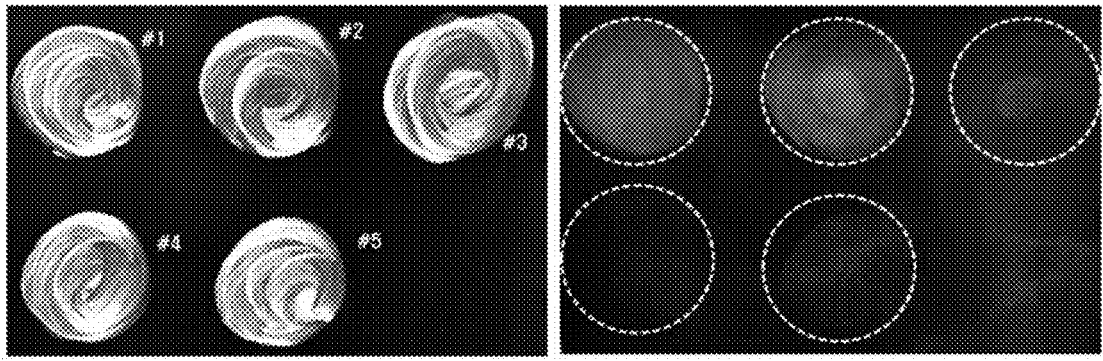
FIG. 3 shows a result of evaluating the easiness of cleansing of the compositions #1 to #5.

Hereinafter, the present disclosure will be described in detail through examples, etc. to help understanding. However, the examples of the present disclosure may be modified in various different forms, and the scope of the present disclosure should not be construed as being limited to the following examples. The examples of the present disclosure are provided to more completely explain the present disclosure to those having ordinary knowledge in the art.

Experiment 1. Variation of Fatty Acid Contents

Makeup products for skin tone correction with the formulas and contents described in Table 1 were prepared as follows.

The components described in A were weighed according to the contents and dissolved completely by heating to 70-80° C. The components described in B were dispersed completely and heated to 70-80° C. A was slowly added to B while emulsifying for 5 minutes, and the prepared emulsion was cooled to 30° C.

In Table 1, the pigment X was a mixture of a titanium dioxide powder (LP-TR 10, Miyoshi) coated with a mixture of aluminum hydroxide, lipoamino acid and palmitic acid; red iron oxide (OTS Red R-516, Daito Kasei Kogyo); yellow iron oxide (OTS-2 Yellow LLXILO, Daito Kasei Kogyo); and black iron oxide (OTS-2 lack BL-100, Daito Kasei Kogyo). The weight ratio of the mixture was 93.482: 1.080:5.400:0.038 (coated $TiO_2$:red iron oxide:yellow iron oxide:black iron oxide). The lipoamino acid was a mixture of palmitoyl proline, magnesium palmitoyl glutamate and sodium palmitoyl sarcosinate, and the coated titanium dioxide powder had a mode value of 357 nm and a median ($D_{50}$) value of 434 nm according to the data provided by the manufacturer. The prepared composition was dispersed in ethanol and analyzed using a laser particle size analyzer.

TABLE 1

| (Unit: wt % ) | | #1 | #2 | #3 | #4 | #5 |
|---|---|---|---|---|---|---|
| A | Water | 28 | 28 | 28 | 28 | 28 |
| | Sodium chloride | 2 | 2 | 2 | 2 | 2 |
| | Glycerin | 10 | 10 | 10 | 10 | 10 |
| B | Cyclopentasiloxane | 20 | 20 | 20 | 20 | 20 |
| | Phenyl trimethicone | 5 | 5 | 5 | 5 | 5 |
| | Cetyl ethylhexanoate | 15 | 14 | 11 | 7 | 0 |
| | Isostearic acid | 0 | 1 | 4 | 8 | 15 |
| | Ethylhexyl methoxycinnamate | 5 | 5 | 5 | 5 | 5 |
| | PEG 10 dimethicone | 5 | 5 | 5 | 5 | 5 |
| | Pigment X | 10 | 10 | 10 | 10 | 10 |
| | Total | 100 | 100 | 100 | 100 | 100 |

Water resistance was evaluated by the following method.

25 mg of the cosmetic composition was applied onto a black rubber plate. Tap water run over the area where the composition was applied for 15 seconds or longer, and the degree of washing off was checked. The result is shown in FIG. 2.

Easiness of cleansing was evaluated by the following method.

25 mg of the cosmetic composition was applied onto a black rubber plate. After dropping 4-5 drops of diluted 20% cleansing foam thereon and rubbing sufficiently, it was rinsed with running water and the degree of washing off was compared. As the cleansing foam, commercially available Lacvert BRI:D cleansing foam was used. The pH of the diluted 20% cleansing foam was 9.5. The result is shown in FIG. 3.

As shown in FIG. 2, all the compositions of the present disclosure showed superior water resistance, without being washed off by tap water. That is to say, the water resistance of the W/O compositions did not decrease even when the fatty acids were contained.

In contrast, as shown in the result of the evaluation of easiness of cleansing in FIG. 3, the makeup cosmetic products containing 1 wt % or more of fatty acids were washed off better. It is though that the fatty acid helps in cleansing through saponification under the high pH condition such as soapy water. However, the present disclosure is not limited to the theoretical mechanism.

Experiment 2. Variation of Fatty Acids

Makeup cosmetic products were prepared in the same manner as in Experiment 1, and water resistance and easiness of cleansing were evaluated.

TABLE 2

| (Unit: wt %) | | #11 | #12 | #13 | #14 | #15 |
|---|---|---|---|---|---|---|
| A | Water | 28 | 28 | 28 | 28 | 28 |
| | Sodium chloride | 2 | 2 | 2 | 2 | 2 |
| | Glycerin | 10 | 10 | 10 | 10 | 10 |
| B | Cyclopentasiloxane | 20 | 20 | 20 | 20 | 20 |
| | Phenyl trimethicone | 5 | 5 | 5 | 5 | 5 |
| | Cetyl ethylhexanoate | 5 | 5 | 5 | 5 | 5 |
| | Myristic acid | 10 | | | | |
| | Palmitic acid | | 10 | | | |
| | Stearic acid | | | 10 | | |
| | Isostearic acid | | | | 10 | |
| | Behenic acid | | | | | 10 |
| | Ethylhexyl methoxycinnamate | 5 | 5 | 5 | 5 | 5 |
| | PEG 10 dimethicone | 5 | 5 | 5 | 5 | 5 |
| | Pigment X | 10 | 10 | 10 | 10 | 10 |
| | Total | 100 | 100 | 100 | 100 | 100 |

Figure 4:
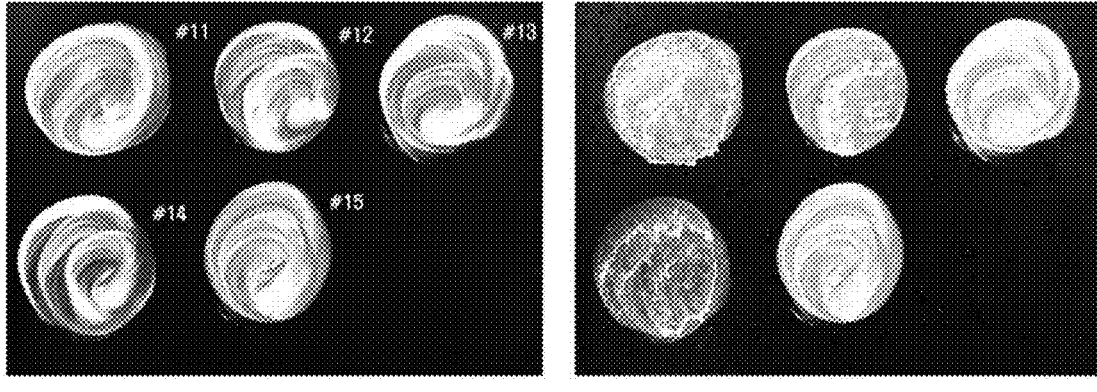
FIG. 4 shows a result of evaluating the water resistance of compositions #11 to #15.
Figure 5:
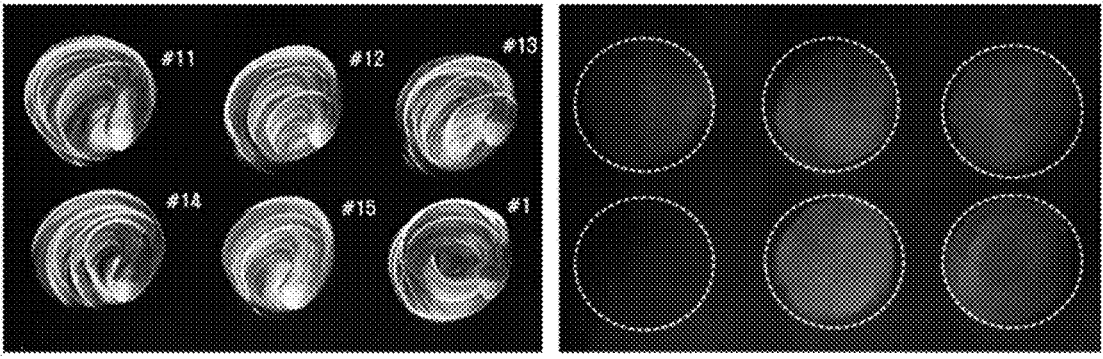
FIG. 5 shows a result of evaluating the easiness of cleansing of the compositions #11 to #15.

Water resistance was evaluated in the same manner as in Experiment 1 and the result is shown in FIG. 4. Easiness of cleansing was evaluated in the same manner as in Experiment 1 and the result is shown in FIG. 5.

As a result of the experiment, all the compositions showed superior water resistance regardless of the fatty acids. In contrast, for the easiness of cleansing, the effect of isostearic acid (#14) was remarkably superior as compared to other solid fatty acids.

Experiment 3. Variation of Pigment-Grade Powders

Makeup cosmetic products were prepared in the same manner as in Experiment 1, and water resistance and easiness of cleansing were evaluated.

The pigment X in Table 3 was the same as that described in Table 1.

In Table 3, the pigment Y was a mixture of a titanium dioxide powder (SiTiO$_2$ CR50, Korea Fuji Chemical Engineering) coated with aluminum hydroxide and dimethicone; red iron oxide; black iron oxide; and yellow iron oxide. The mixing ratio was 93.482:1.080:5.4:0.038. The powder size was 250 nm. For reference, SiTiO$_2$ CR50 is a powder obtained by coating TiO$_2$ CR50 with silicon. CR50 is the most common pigment-grade powder with a particle size of 250 nm.

8

TABLE 3

| (Unit: wt %) | | #6 | #7 | #8 | #9 | #10 |
|---|---|---|---|---|---|---|
| A | Water | 28 | 28 | 28 | 28 | 28 |
| | Sodium chloride | 2 | 2 | 2 | 2 | 2 |
| | Glycerin | 10 | 10 | 10 | 10 | 10 |
| B | Cyclopentasiloxane | 20 | 20 | 20 | 20 | 20 |
| | Phenyl trimethicone | 5 | 5 | 5 | 5 | 5 |
| | Cetyl ethylhexanoate | 7 | 7 | 7 | 7 | 7 |
| | Isostearic acid | 8 | 8 | 8 | 8 | 8 |
| | Ethylhexyl methoxycinnamate | 5 | 5 | 5 | 5 | 5 |
| | PEG 10 dimethicone | 5 | 5 | 5 | 5 | 5 |
| | Pigment X | 8 | 6 | 4 | 2 | |
| | Pigment Y | 2 | 4 | 6 | 8 | 10 |
| | Total | 100 | 100 | 100 | 100 | 100 |

Figure 6:
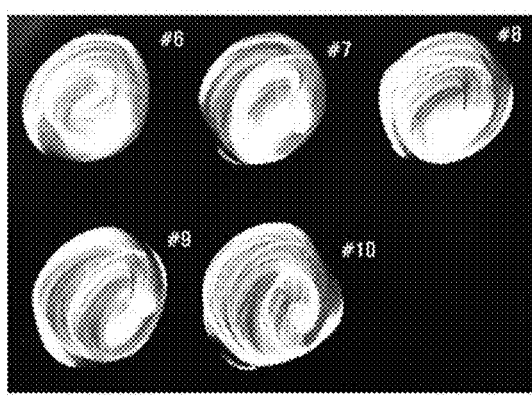
FIG. 6 shows a result of evaluating the water resistance of compositions #6 to #10.
Figure 6:
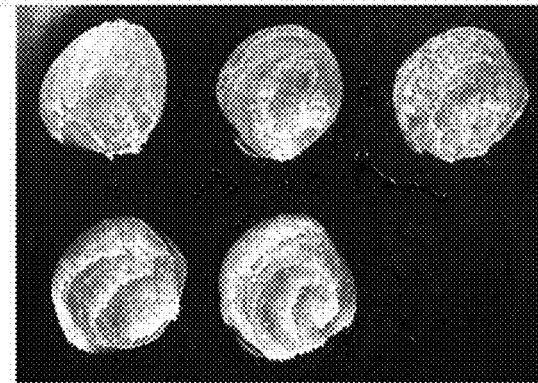
Figure 7:
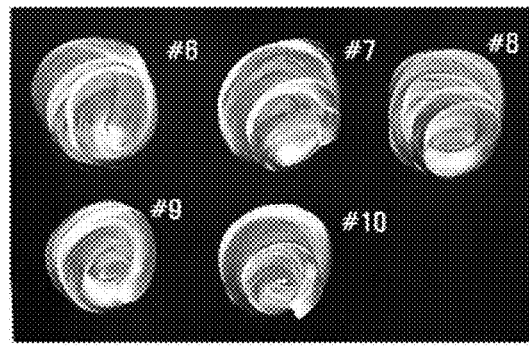
FIG. 7 shows a result of evaluating the easiness of cleansing of the compositions #6 to #10.
Figure 7:
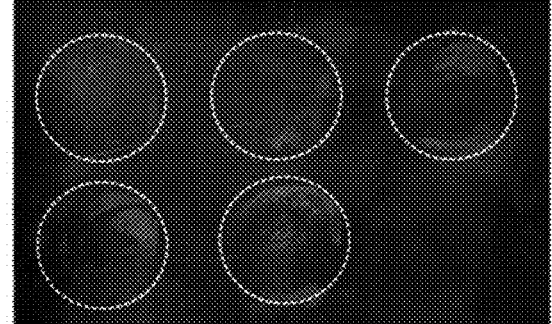

Water resistance was evaluated in the same manner as in Experiment 1 and the result is shown in FIG. 6. Easiness of cleansing was evaluated in the same manner as in Experiment 1 and the result is shown in FIG. 7.

As a result of the experiment, all the compositions showed superior water resistance regardless of the pigments. In contrast, the easiness of cleansing was improved further when the lipoamino acid-coated powder was contained (e.g., 5 wt % or higher; for the sample #8, 6 wt % of the pigment X was used and the content of the lipoamino acid-coated powder in the pigment X was approximately 93.4%).

Experiment 4. Effect of Divalent Ionic Salts

Makeup cosmetic products were prepared in the same manner as in Experiment 1, and water resistance, easiness of cleansing and stability were evaluated.

TABLE 4

| (Unit: wt %) | | #16 | #17 | #18 | #19 | #20 |
|---|---|---|---|---|---|---|
| A | Water | 38.1 | 36.1 | 37.6 | 36.1 | 36.1 |
| | Butylene glycol | 10 | 10 | 10 | 10 | 10 |
| | Magnesium sulfate | | 2 | | | |
| | Sodium chloride | | | 0.5 | 2 | 2 |
| B | Cyclopentasiloxane | 4 | 4 | 4 | 4 | 4 |
| | Isododecane | 8 | 8 | 8 | 8 | 8 |
| | Isostearic acid | 5 | 5 | 5 | 5 | 5 |
| | Ethylhexyl methoxycinnamate | 7 | 7 | 7 | 7 | 7 |
| | Isoamyl p-methoxycinnamate | 7 | 7 | 7 | 7 | 7 |
| | Bis-ethylhexyloxyphenol methoxyphenyl triazine | 1 | 1 | 1 | 1 | 1 |
| | Diethylamino hydroxybenzoyl hexyl benzoate | 4 | 4 | 4 | 4 | 4 |
| | Sorbitan olivate | 4 | 4 | 4 | 4 | 4 |
| | PEG-30 dipolyhydroxystearate | 0.3 | 0.3 | 0.3 | 0.3 | 0.3 |
| | Cetyl PEG/PPG-10/1 dimethicone | 0.1 | 0.1 | 0.1 | 0.1 | 0.1 |
| | Disteardimonium hectorite | 1.5 | 1.5 | 1.5 | 1.5 | 1.5 |
| | Zinc oxide | 3 | 3 | 3 | 3 | |
| | Pigment X | 7 | 7 | 7 | 7 | 7 |
| | Total | 100 | 100 | 100 | 100 | 100 |

Figure 8:
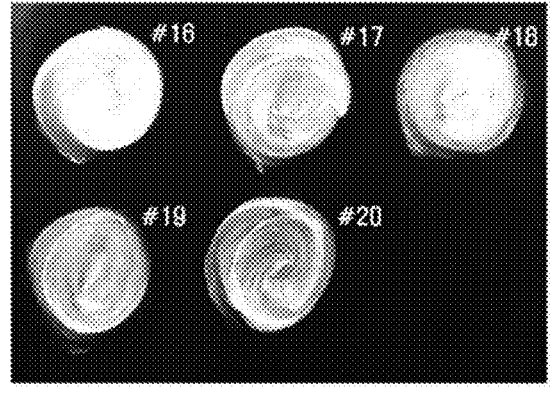
FIG. 8 shows a result of evaluating the water resistance of compositions #16 to #20.
Figure 8:
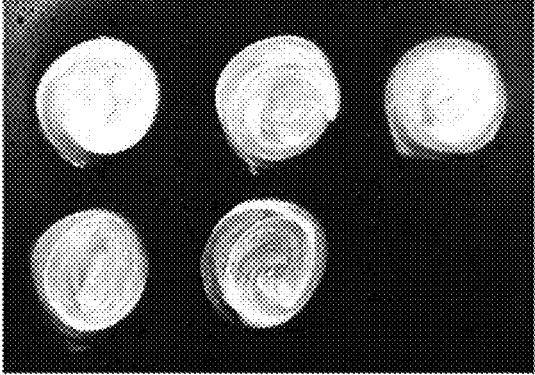
Figure 9:
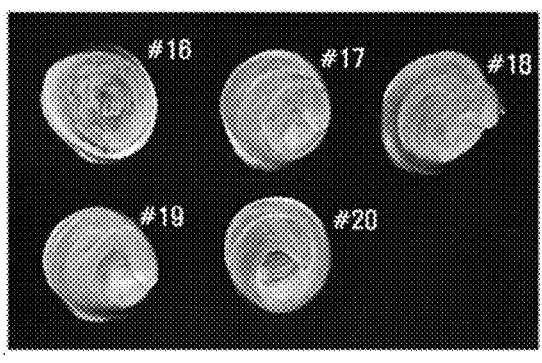
FIG. 9 shows a result of evaluating the easiness of cleansing of the compositions #16 to #20.
Figure 9:
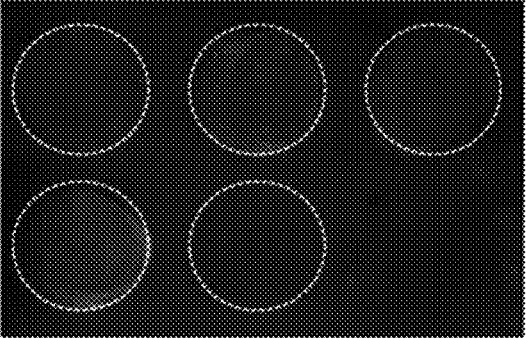

Water resistance was evaluated in the same manner as in Experiment 1 and the result is shown in FIG. 8. Easiness of cleansing was evaluated in the same manner as in Experiment 1 and the result is shown in FIG. 9.

In addition, stability was also evaluated and the result is shown in Table 5.

TABLE 5

|  | #16 | #17 | #18 | #19 | #20 |
|---|---|---|---|---|---|
| Salt | None | $MgSO_4$ 2 wt % | NaCl 0.5 wt % | NaCl 2 wt % | NaCl 2 wt % |
| ZnO | 3 wt % | 3 wt % | 3 wt % | 3 wt % | None |
| Easiness of cleansing | Δ | Δ | Δ | Δ | ○ |
| Stability | X | ○ | Δ | ○ | ○ |

(In Table 5, O indicates superior stability, Δ indicates intermediate stability, and X indicates poor stability.)

As a result of the experiment, all the compositions #16 to #20 showed superior water resistance and easiness of cleansing. In particular, in terms of the easiness of cleansing, the composition #20 containing no divalent ionic salt at all showed the most superior effect better than the compositions #16 to #19 containing divalent ionic salts.

More specifically, as a result of the experiment on the compositions #16 to #20, it was found out that the compositions #16 to #19 containing divalent ionic salts showed slightly decreased cleansing power. The samples containing divalent ionic salts could be removed only when rubbed for a long time with the 20% cleansing foam solution and they remained slightly even after the cleansing. In contrast, the sample #20 could be removed easily and completely and also exhibited superior stability.

What is claimed is:

1. A water-in-oil makeup cosmetic composition comprising isostearic acid, a pigment-grade powder, a monovalent ionic salt, and an emulsifier having an HLB greater than 0 and lower than or equal to 8,
  wherein the pigment-grade powder is a pigment-grade powder coated with a lipoamino acid, and
  wherein the isostearic acid is present in an amount of 3-40 wt % based on the total weight of the composition,
  wherein the pigment-grade powder coated with the lipoamino acid has oil-dispersible properties at pH 7 and water-dispersible properties at pH 10, and wherein the pigment-grade powder is comprised in an amount of 5-40 wt % based on the total weight of the composition.

2. The makeup cosmetic composition according to claim 1, wherein the lipoamino acid is palmitoyl proline, magnesium palmitoyl glutamate, sodium palmitoyl sarcosinate, or a mixture thereof.

3. The makeup cosmetic composition according to claim 1, wherein the pigment-grade powder is $TiO_2$ coated with a lipoamino acid.

4. The makeup cosmetic composition according to claim 1, wherein the pigment-grade powder has a powder size of 200-1000 nm.

5. The makeup cosmetic composition according to claim 1, wherein the monovalent ionic salt is sodium chloride.

6. A water-in-oil makeup cosmetic composition comprising isostearic acid, a pigment-grade powder, a monovalent ionic salt, and an emulsifier having an HLB greater than 0 and lower than or equal to 8,
  wherein the pigment-grade powder is a pigment-grade powder coated with a lipoamino acid,
  wherein the isostearic acid is present in an amount of 3-40 wt % based on the total weight of the composition,
  wherein the pigment-grade powder coated with the lipoamino acid has oil-dispersible properties at pH 7 and water-dispersible properties at pH 10, and is comprised in an amount of 5-40 wt % based on the total weight of the composition, and
  wherein the composition comprises 5 wt % or less of ZnO based on the total weight of the composition.

7. The makeup cosmetic composition according to claim 6, wherein the lipoamino acid is palmitoyl proline, magnesium palmitoyl glutamate, sodium palmitoyl sarcosinate, or a mixture thereof.

8. The makeup cosmetic composition according to claim 6, wherein the pigment-grade powder is $TiO_2$ coated with a lipoamino acid.

9. The makeup cosmetic composition according to claim 6, wherein the pigment-grade powder has a powder size of 200-1000 nm.

10. The makeup cosmetic composition according to claim 6, wherein the monovalent ionic salt is sodium chloride.

11. The makeup cosmetic composition according to claim 1, wherein the isostearic acid is present in an amount of 5-40 wt % based on the total weight of the composition.

12. The makeup cosmetic composition according to claim 6, wherein the isostearic acid is present in an amount of 5-40 wt % based on the total weight of the composition.

* * * * *